US012797582B2

(12) United States Patent
Pope et al.

(10) Patent No.: US 12,797,582 B2
(45) Date of Patent: Nov. 17, 2026

(54) UNIFORM OUTER DIAMETER GUIDEWIRE DEVICES

(71) Applicant: SCIENTIA VASCULAR, INC., West Valley City, UT (US)

(72) Inventors: Brandon Rodney Pope, Salt Lake City, UT (US); William Rigby Eccles, Centerville, UT (US)

(73) Assignee: SCIENTIA VASCULAR, INC., West Valley City, UT (US)

( * ) Notice: Subject to any disclaimer, the term of this patent is extended or adjusted under 35 U.S.C. 154(b) by 337 days.

(21) Appl. No.: 18/391,400

(22) Filed: Dec. 20, 2023

(65) Prior Publication Data

US 2024/0207577 A1 Jun. 27, 2024

Related U.S. Application Data

(60) Provisional application No. 63/434,432, filed on Dec. 21, 2022.

(51) Int. Cl.
*A61M 25/01* (2006.01)
*A61M 25/09* (2006.01)

(52) U.S. Cl.
CPC ........ *A61M 25/0141* (2013.01); *A61M 25/09* (2013.01); *A61M 2025/09075* (2013.01); *A61M 2025/09133* (2013.01)

(58) Field of Classification Search
CPC ............ A61M 25/09; A61M 25/09016; A61M 25/09025; A61M 25/09033; A61M 2025/09058; A61M 2025/09075–09091; A61M 2025/0915; A61M 2025/09166
USPC .......................................................... 600/585
See application file for complete search history.

(56) References Cited

U.S. PATENT DOCUMENTS

| | | | | | |
|---|---|---|---|---|---|
| 4,800,890 | A | | 1/1989 | Cramer | |
| 5,111,829 | A | * | 5/1992 | Alvarez de Toledo .. | A61B 1/01 600/585 |
| 5,385,152 | A | * | 1/1995 | Abele ................... | A61M 29/00 606/191 |
| 5,452,726 | A | * | 9/1995 | Burmeister ........... | A61M 25/09 604/529 |
| D363,544 | S | | 10/1995 | Rowland et al. | |
| D363,776 | S | | 10/1995 | Rowland et al. | |
| 5,749,837 | A | * | 5/1998 | Palermo ................ | A61M 25/09 600/585 |

(Continued)

FOREIGN PATENT DOCUMENTS

JP 2009515656 A * 4/2009 ............. A61L 29/14

OTHER PUBLICATIONS

English Machine Translation of JP-2009515656-A (Year: 2009).*

(Continued)

*Primary Examiner* — Adam J Eiseman
(74) *Attorney, Agent, or Firm* — Workman Nydegger

(57) ABSTRACT

Disclosed are intravascular devices for navigating tortuous vascular environments like the human brain. The disclosed guidewire includes a core wire, a first tube within which the distal section of the core is inserted, and a second tube within which the proximal section of the core is inserted. The first and second tubes have a substantially similar outer diameter such that the guidewire has a uniform outer diameter over its complete length for effective catheter tracking over the guidewire.

19 Claims, 2 Drawing Sheets

(56) References Cited

U.S. PATENT DOCUMENTS 5,836,893 A * 11/1998 Urick .................... A61M 25/09 600/585
5,876,356 A * 3/1999 Viera .................... A61M 25/09 600/585
6,027,863 A 2/2000 Donadio, III
6,142,975 A * 11/2000 Jalisi ........................ C21D 7/02 604/170.01
D435,909 S 1/2001 Ogino et al.
6,428,489 B1 8/2002 Jacobsen et al.
6,579,246 B2 6/2003 Jacobsen et al.
7,172,587 B2 2/2007 Poole et al.
7,278,973 B2 * 10/2007 Iwami .................. A61M 25/09 600/585
D598,094 S 8/2009 Alber
D611,596 S 3/2010 Kousai et al.
8,007,434 B2 8/2011 Olson
8,048,004 B2 11/2011 Davis et al.
8,092,444 B2 1/2012 Lentz et al.
8,257,279 B2 9/2012 Davis et al.
8,292,827 B2 10/2012 Musbach et al.
8,376,865 B2 2/2013 Forster et al.
8,409,114 B2 4/2013 Parins
8,460,213 B2 6/2013 Northrop
8,465,469 B2 6/2013 Brightbill
8,540,668 B2 9/2013 Griffin et al.
8,551,021 B2 10/2013 Voeller et al.
8,556,914 B2 10/2013 Vrba
8,585,643 B2 11/2013 Vo et al.
8,784,337 B2 7/2014 Voeller et al.
8,795,254 B2 8/2014 Layman et al.
8,900,163 B2 12/2014 Jacobsen et al.
8,915,865 B2 12/2014 Jacobsen et al.
8,932,235 B2 1/2015 Jacobsen et al.
8,936,558 B2 1/2015 Jacobsen et al.
9,011,511 B2 4/2015 Gregorich et al.
9,072,874 B2 7/2015 Northrop et al.
D742,000 S 10/2015 Kanazawa
9,162,040 B2 10/2015 Vo et al.
9,227,037 B2 1/2016 Northrop
9,375,234 B2 6/2016 Vrba
9,433,762 B2 9/2016 Griffin et al.
9,439,557 B2 9/2016 Boulais
9,808,595 B2 11/2017 Turnlund et al.
9,839,764 B2 12/2017 Chouinard
D809,138 S 1/2018 Khan et al.
9,999,748 B2 6/2018 Cajamarca et al.
10,028,666 B2 7/2018 Gregorich
10,052,013 B2 8/2018 Boulais
10,149,608 B2 12/2018 Fujitani
D839,426 S 1/2019 Bajwa
D847,335 S 4/2019 Kuwada
10,252,024 B2 4/2019 Northrop et al.
10,300,249 B2 5/2019 Tao et al.
D855,180 S 7/2019 Haefliger
10,350,383 B2 7/2019 Shuman
D855,800 S 8/2019 Gabay et al.
10,420,537 B2 9/2019 Salahieh et al.
10,456,556 B2 10/2019 Cabiri
10,675,444 B2 6/2020 Kauphusman et al.
10,758,710 B2 9/2020 Romano
10,806,893 B2 10/2020 Jaroch
11,007,345 B2 5/2021 Cottone
11,052,226 B2 7/2021 Salahieh et al.
11,141,566 B2 10/2021 Cabiri
D946,148 S 3/2022 Takemoto
11,278,704 B2 3/2022 Pleijers
11,383,068 B2 7/2022 Tran et al.
11,426,560 B2 * 8/2022 Telang .................. A61M 25/09
11,471,645 B2 10/2022 Mcniven et al.
11,497,512 B2 11/2022 Wallace et al.
11,565,093 B2 1/2023 Kirt et al.
D980,427 S 3/2023 Method et al.
11,679,236 B2 6/2023 Von et al.
11,724,065 B2 8/2023 Tilson et al.
11,724,068 B2 8/2023 Von et al.
11,759,217 B2 9/2023 Keating et al.
11,766,539 B2 9/2023 Yee et al.
D1,014,751 S 2/2024 Shih
11,896,757 B2 2/2024 Tran et al.
11,918,753 B2 3/2024 Moquin et al.
11,957,312 B2 4/2024 Boulais
2004/0167439 A1 * 8/2004 Sharrow ............... A61M 25/09 600/585
2008/0312597 A1 * 12/2008 Uihlein ................. A61M 25/09 604/164.13
2009/0112127 A1 4/2009 Keating et al.
2010/0069794 A1 3/2010 Uihlein
2015/0148706 A1 5/2015 Abner
2016/0287054 A1 10/2016 Fujitani
2016/0310702 A1 10/2016 Cabiri
2017/0049594 A1 2/2017 Banas et al.
2018/0071496 A1 3/2018 Snyder et al.
2019/0290883 A1 * 9/2019 Lippert ............. A61M 25/0051
2019/0358434 A1 11/2019 Fuller et al.
2020/0222666 A1 7/2020 Chan et al.
2020/0330734 A1 10/2020 Sugita et al.
2021/0283372 A1 9/2021 Murphy
2022/0039644 A1 2/2022 Dayton et al.
2022/0047845 A1 2/2022 Niederhauser et al.
2022/0105312 A1 4/2022 Davis
2022/0176075 A1 6/2022 Mcdermott et al.
2022/0218358 A1 7/2022 Dagan et al.
2022/0273474 A1 9/2022 Koop et al.
2022/0323166 A1 10/2022 Tilson et al.
2023/0010697 A1 1/2023 Sharma et al.
2023/0069698 A1 3/2023 Hallauer et al.
2023/0285720 A1 9/2023 Isogai
2023/0405276 A1 12/2023 Cabiri

OTHER PUBLICATIONS

International Search Report and Written Opinion received for PCT Patent Application No. PCT/US23/085351, mailed on May 22, 2024, 11 pages.

* cited by examiner

UNIFORM OUTER DIAMETER GUIDEWIRE DEVICES

CROSS-REFERENCE TO RELATED APPLICATIONS

This application claims the benefit of and priority to U.S. Provisional Application No. 63/434,432, filed Dec. 21, 2022 and titled "MICRO-FABRICATED GUIDEWIRE DEVICES HAVING VARYING DIAMETERS MADE UNIFORM," the entirety of which is incorporated herein by reference.

BACKGROUND

Guidewire devices are often used to lead or guide catheters or other interventional devices to a targeted anatomical location within a patient's body. Typically, guidewires are passed into and through a patient's vasculature in order to reach the target location, which may be at or near the patient's heart or brain, for example. Radiographic imaging is typically utilized to assist in navigating a guidewire to the targeted location. In many instances, a guidewire is placed within the body during the interventional procedure where it can be used to guide multiple catheters or other interventional devices to the targeted anatomical location.

Guidewires are available with various outer diameter sizes. Widely utilized sizes include 0.010, 0.014, 0.016, 0.018, 0.024, 0.035, and 0.038 inches, for example, though they may also be smaller or larger in diameter. Because torque transmission is a function of diameter, larger diameter guidewires typically have greater torque transmission (the ability to effectively transfer torque from proximal portions of the wire to more distal portions of the wire). On the other hand, smaller diameter guidewires typically have greater flexibility.

A catheter used in conjunction with a guidewire will be sized with an inner diameter somewhat larger than the outer diameter of the guidewire to enable the catheter to be positioned over and translated upon the guidewire. The difference in size between the guidewire and catheter can affect the ability of the catheter to travel along the guidewire. For example, the larger the annular space between the outer diameter of the guidewire and the inner diameter of the catheter, the greater the amount of radial play the catheter may experience and the more difficult it may be to navigate the catheter over the guidewire. With excessive radial play, the distal end of the catheter may have a higher risk of catching against vasculature or other anatomy of the patient rather than smoothly following along the guidewire path.

Often, a guidewire size is selected to minimize the amount of annular space between the guidewire and a given catheter size required or desired for a particular procedure, and to thereby limit the types of issues described above. Some devices include a flexible elongated member extending along and encompassing the distal section of the guidewire with an outer diameter near that of the inner diameter of the catheter so as to reduce radial play. However, a challenge exists in that a catheter has a propensity to catch on the elongated member when translating from the proximal section to the distal section of the guidewire. A guidewire wherein the proximal section has a substantially similar diameter as the elongated member would help to ameliorate the propensity of the catheter to catch at the proximal-distal transition of the guidewire. However, previous designs have not been able to do so without sacrificing flexibility or tensional transmission.

What is needed, therefor, is a guidewire device capable of being manufactured with a relatively large outer diameter along the complete length of the guidewire, that minimizes the annular space between the guidewire and certain sizes of compatible catheters, and that is also capable of providing sufficient flexibility and torquability. A catheter would more easily travel along such a guidewire, decreasing surgical complications, potential injury, and operation time.

SUMMARY

Disclosed is an intravascular device, comprising a core having a proximal and a distal section, a first tube having a proximal and a distal section wherein the first tube is coupled to the core such that the distal section of the core passes into and is encompassed by the tube structure of the first tube, and a second tube having substantially the same outer diameter as the first tube, wherein the second tube is coupled to the core such that the proximal section of the core passes into and is encompassed by the tube structure of the second tube. Optionally, a portion of the proximal section of the first tube passes into and is encompassed by the second tube.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

Overview of Guidewire Structural Features

Figure 1:
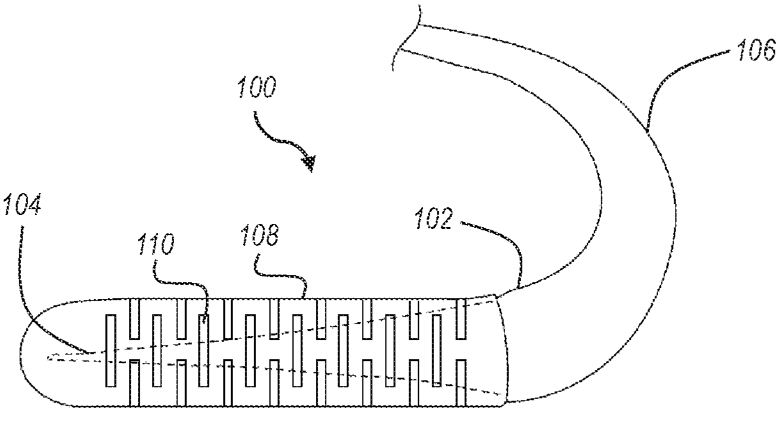
FIG. 1 illustrates an embodiment of a guidewire device having a core and a tube coupled to the distal section of the core.

FIG. 1 schematically illustrates a guidewire device 100 suitable for utilizing one or more features of the present disclosure. The illustrated guidewire 100 includes a core 102 and an outer tube 108. The core 102 includes a distal section 104 that extends into the outer tube 108 as shown. The distal section 104 may be tapered, either continuously or in one or more discrete sections, so that the more distal sections have a smaller diameter and greater flexibility than more proximal sections. For example, the distal section 104 may be ground so as to progressively taper to a smaller diameter at the distal end. In some embodiments, the distal section 104 may be flattened into a ribbon-like shape with a flat, rectangular, or oblong cross section.

The core 102 and the tube 108 are typically formed from different materials. For example, the tube 108 is preferably formed from a relatively flexible and elastic material such as nitinol, whereas the core 102 may be formed from a relatively less flexible and less elastic material such as stainless steel. Forming the core 102 from stainless steel may be advantageous because it allows the distal tip to hold a shape when selectively bent/shaped by an operator and because stainless steel provides sufficient modulus of elasticity to provide more responsive translational movement. While these materials are presently preferred, other suitable materials such as polymers or other metals/alloys may also be utilized.

The tube 108 is coupled to the core 102 (e.g., using adhesive, soldering, and/or mechanical fixture) in a manner that beneficially allows torsional forces to be transmitted from the core 102 to the tube 108 and thereby to be further transmitted distally by the tube 108. A medical grade adhesive or other suitable material may be used to couple the tube 108 to the core wire 102 at the distal end of the device to form an atraumatic covering.

The outer tube 108 may include a cut pattern that forms fenestrations 110 in the tube 108. The pattern of fenestrations 110 can include axially extending "beams" and circumferentially extending "rings" as shown, and/or may be arranged to provide desired flexibility characteristics to the tube 108, including the promotion of preferred bending directions, the reduction or elimination of preferred bending directions, or gradient increases in flexibility along the longitudinal axis, for example. Examples of cut patterns and other guidewire device features that may be utilized in the guidewire devices described herein are provided in detail in U.S. Pat. No. 11,369,351, which is incorporated herein by reference in its entirety. Other slot or fenestration patterns may additionally or alternatively be utilized.

The guidewire device 100 can have a length for reaching to a targeted anatomical area. The guidewire device 100 typically has a length ranging from about 50 cm to about 350 cm depending on particular application needs. The tube 108 may have a length ranging from about 20 cm to about 65 cm, more typically about 30 cm to about 55 cm, such as about 35 cm to about 45 cm.

The guidewire device 100 may have a diameter of about 0.014 inches to about 0.035 inches, though larger or smaller sizes may also be utilized depending on particular application needs, and the features of the present disclosure are not necessarily limited to certain guidewire sizes. Some embodiments may have outer diameter sizes corresponding to standard guidewire sizes such as 0.014 inches, 0.016 inches, 0.018 inches, 0.024 inches, 0.035 inches, or other such sizes common to guidewire devices.

The distal section 104 of the core 102 may taper to a diameter of about 0.002 inches, or a diameter within a range of about 0.001 to 0.005 inches. In some embodiments, the distal tip may be flattened (e.g., to a rectangular cross section) to further enhance bending flexibility while minimizing reductions in cross-sectional area needed for tensile strength. In such embodiments, the cross section may have dimensions of about 0.001 inches by 0.003 inches, for example. In some embodiments, the tube 108 has a length within a range of about 3 to 100 cm.

Figure 2:
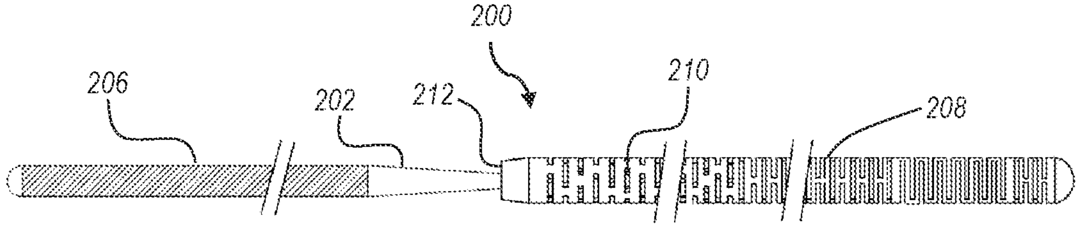
FIG. 2 illustrates an embodiment of a guidewire device having a core and a tube coupled to the distal section of the core, the proximal end of the tube creating a ledge.

FIG. 2 illustrates an example of a guidewire 200. Guidewire 200 may include any of the general features described above in relation to guidewire 100. As shown, the guidewire 200 includes a core 202 and an outer tube 208. The outer tube 208 includes a plurality of fenestrations 210. A polymer-based adhesive may form an atraumatic distal tip.

The core 202 also includes a proximal section 206 (synonymously referred to herein as the proximal core 206) that is disposed proximal of the outer tube 208 and is not inserted into the outer tube 208. The proximal core 206 may comprise a friction-lowering coating, such as polytetrafluoroethylene (PTFE) and/or other suitable coating materials. The tube 208 may also include a coating, preferably a suitable hydrophilic coating.

As shown, the outer diameter of the tube 208 may be larger than the outer diameter of the proximal core 206. In one example, the proximal core 206 has an outer diameter of about 0.018 inches, while the tube 208 has an outer diameter of about 0.024 inches. Other core and/or tube sizes may also be utilized, however. For example, the tube 208 may have an outer diameter that is about 15% to about 50% larger than the outer diameter of the proximal core 206, or about 20% to about 45% larger, or about 25% to about 40% larger, such as about 30% to about 35% larger.

Differentially Sized Core and Tube

As mentioned above, a larger outer diameter in the tube 208 can better match certain desired catheter sizes and thereby reduce the amount of annular space between the guidewire and catheter during placement of the catheter over the guidewire. A larger outer diameter of the tube 208 reduces the likelihood the catheter will catch on the patient's vasculature. This is particularly beneficial at the more distal sections of the guidewire, which are more likely to be navigated through deeper, more tortuous portions of the patient's vasculature.

However, increasing the diameter of the proximal section 206 of the core 202 to match the larger diameter of the tube 208 may make the core 202 too stiff for use in certain desired applications. Thus, maintaining a smaller proximal section 206 of the core 202, while increasing the size of the tube 208 relative to the core 202, allows use of the more flexible core 202 while still enabling the benefits of a larger tube 208 at the distal sections of the guidewire 200.

However, because tube 208 may have a significantly larger diameter than core 202, a ledge 212 may form at the proximal end of tube 208, as shown in FIG. 2. Such a ledge 212 may present a particular obstacle to proper handling of the catheter and prevent smooth tracking of the catheter along the guidewire device 200. This disruption to the control of the catheter can raise the risk of interventional procedure delays, suboptimal outcomes, inability to access the target location, or even tissue injury. Therefore, a uniform diameter extending the complete length of the guidewire device 200 over which a catheter may be smoothly navigated may present real benefits for patient outcomes.

Guidewire Devices with Uniform Diameters

Figure 3:
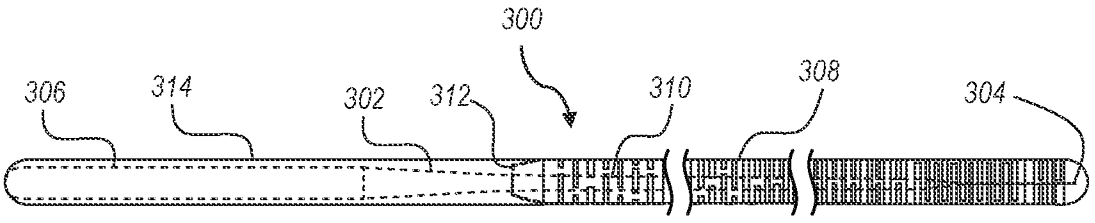
FIG. 3 illustrates an embodiment of a guidewire device having a core, a first tube coupled to the distal section of the core, and a second tube coupled to the proximal section of the core, the distal end of the second tube encompassing the proximal end of the first tube.

FIG. 3 illustrates an example of a guidewire 300. The guidewire 300 may also include any of the general features described above in relation to guidewires 100 and 200, with like reference numbers indicating like parts. As shown, the guidewire 300 includes a core 302 and a first tube 308, with a distal section 304 of the core 302 inserted into the first tube 308. The first tube 308 includes a plurality of fenestrations 310.

Also illustrated is a second tube 314 encompassing the proximal section 306 of the core 302. The proximal section 306 of the core 302 is the portion that extends proximally from the first tube 308. The second tube 314 has a substantially similar outer diameter as the first tube 308. In some embodiments, as shown, the proximal end of the first tube 308 passes into and is encompassed by the distal end of the second tube 314 (or vice versa) such that a seamless transition is made from the second tube 314 to the first tube 308 without a significant change in outer diameter. Additionally, the second tube 314 may extend to the proximal end of the core 302, such that the diameter of the guidewire device 300 is substantially uniform along its complete length.

In some embodiments, the second tube 314 is formed from a relatively flexible and elastic material such as nitinol. The second tube 314 may also comprise a friction-lowering coating, such as polytetrafluoroethylene (PTFE) and/or other suitable coating materials. The second tube 314 may also include a coating, preferably a suitable hydrophilic coating. The second tube 314 may be prefabricated and threaded onto the core 302 and then bound to the core 302 using a weld, solder, adhesive, and/or other means of structural attachment.

In alternative embodiments, the second tube 314 is formed from a polymer material and is dip-coated, laminated, or otherwise applied onto the core 302. For example, the second tube 314 may be laminated to the core 302 through a reflow process, including the use of a heat-shrinkable fusing sleeve, such that the material forming the second tube 314 melts and bonds directly to the core 302, reducing the amount of adhesive needed to fabricate the guidewire device 300.

The second tube 314 can have a constant outer diameter, or as shown, a variable inner diameter. That is, the inner diameter can be larger at some points along the length of the second tube 314 and smaller at other points along the length of the second tube 314. A variable inner diameter can be beneficial because it allows close contact with the underlying proximal section 306 of the core 302 even if the proximal section 306 of the core 302 has a variable outer diameter, which can often be the case in order to impart desired flexibility/stiffness profiles and/or because of joints or connections within the structure of the proximal section 306 of the core 302.

Incorporating a second tube 314 on the guidewire device 300 provides several benefits. Because the diameter of the second tube 314 is substantially similar to the diameter of the first tube 308, a catheter will more smoothly track along the guidewire device 300. In particular, the transition from the proximal section to the distal section of the guidewire device 300 is greatly improved by internalizing the ledge 312 created by the first tube 308.

Further, because the second tube 314 comprises a softer material, the improvement in translating the catheter is obtained without compromising the overall flexibility of the guidewire device 300, as would have occurred if the proximal section of the core 302 were simply enlarged. In embodiments where the second tube 314 comprises a friction-lowering or hydrophilic coating, the above benefits are obtained while improving the ability of the guidewire device 300 to pass along and otherwise avoid harming the vasculature of the patient.

Figure 4:
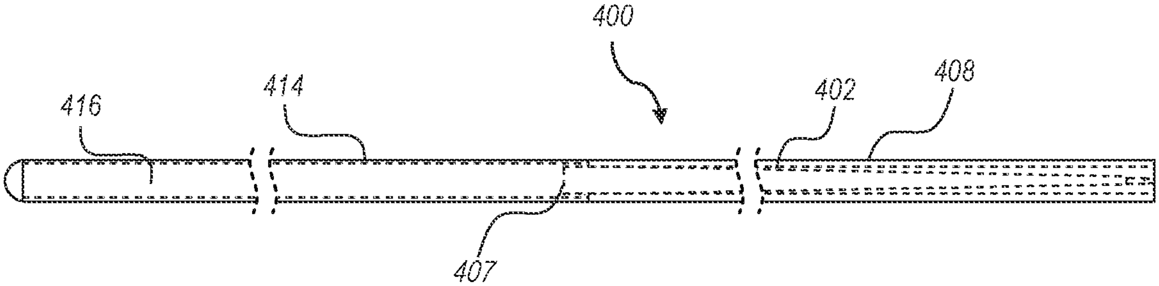
FIG. 4 illustrates an embodiment of a guidewire device having a core, a first tube coupled to the distal section of the core, and a second tube coupled to the proximal section of the core, the proximal section of the core passing into and extending along only a portion of the second tube.

FIG. 4 illustrates another example of a guidewire 400. The guidewire 400 may also include any of the general features described above in relation to guidewires 100, 200, and 300, with like reference numbers indicating like parts. As shown, the guidewire 400 includes a core 402, a first tube 408, and a second tube 414. The first tube 408 may include a plurality of fenestrations (not shown).

In this embodiment, the second tube 414 tube (e.g., a hypotube) may comprise a hollow lumen 416. The proximal end 407 of the core 402 passes into and is encompassed by the distal end of the second tube 414, with the proximal end of the core 402 passing into only a portion of the second tube 414. The distal end of the second tube 414 extends to the proximal end of the first tube 408, creating a smooth transition between the first tube 408 and the second tube 414.

In some embodiments, the proximal end of the first tube 408 may pass into and be encompassed by the distal end of the second tube 414 or vice versa. The proximal end of the core 402 may be secured to the distal end of the second tube 414 using a weld, solder, adhesive, and/or other means of structural attachment. The portion of the second tube 414 that is longitudinally coincident with the core 402 may be only 25% or less of the total length of the second tube 414, such as 20% or less, or 15% or less, or 10% or less, or 5% or less of the total length of the second tube 414.

The second tube 414 may comprise a metal, metal alloy, or other appropriate material suitable for use in a guidewire. Because torque transmission is a function of outer diameter, a metal tube presents comparatively good torsional transmission without suffering increased stiffness and decreased flexibility associated with wires having a solid metal core. A second tube 414 comprising metal may therefore provide suitable torquability, and a balance of stiffness and flexibility while retaining the benefits of a guidewire device 400 with a substantially uniform outer diameter.

The lumen 416 of the second tube 414 may optionally contain a filler used to provide luminal support to the second tube 414. The filler may comprise polyether block amide (PEBA) and/or other polymer, for example. Additionally, or alternatively, the filler may comprise a soft metal, or other material not significantly increasing the stiffness of the guidewire device 400. The filler may have a flexural modulus of approximately 1 MPa to approximately 1000 MPa, or approximately 100 MPa to approximately 900 MPa, or approximately 200 MPa to approximately 800 MPa, or approximately 300 MPa to approximately 700 MPa, or approximately 400 MPa to approximately 600 MPa, or approximately 500 MPa, or a range with endpoints defined by any two of the foregoing values.

Example Embodiments

The following list of clauses represents a non-exhaustive list of example embodiments according to the present disclosure.

Clause 1. An intravascular device, comprising: a core having a proximal section and a distal section; a first tube having a proximal section and a distal section, wherein the first tube is coupled to the core such that the distal section of the core passes into and is encompassed by the first tube; and a second tube having substantially the same outer diameter as the first tube, wherein the second tube is coupled to the core such that the proximal section of the core passes into and is encompassed by the second tube, wherein the second tube extends over at least 50% of the length of the proximal section of the core.

Clause 2. The intravascular device of clause 1, wherein the second tube extends over at least 75% of the length of the proximal section of the core.

Clause 3. The intravascular device of clause 1 or clause 2, wherein the second tube extends over substantially the complete length of the proximal section of the core.

Clause 4. The intravascular device of any preceding clause, wherein at least a portion of the proximal section of the first tube passes into and is encompassed by the second tube.

Clause 5. The intravascular device of any preceding clause, wherein the second tube has a lower elastic modulus than the first tube.

Clause 6. The intravascular device of any preceding clause, wherein the second tube comprises a polymer.

Clause 7. The intravascular device of any preceding clause, wherein the second tube is laminated to the proximal section of the core.

Clause 8. The intravascular device of any preceding clause, wherein the second tube has a variable inner diameter.

Clause 9. The intravascular device of clause 8, wherein the variable inner diameter is larger at a proximal section of the second tube and smaller at a distal section of the second tube.

Clause 10. The intravascular device of any one of clauses 1 through 5, wherein the second tube is optionally formed from metal.

Clause 11. The intravascular device of clause 10, wherein the second tube is a hypotube.

Clause 12. The intravascular device of clause 10 or clause 11, wherein the second tube extends farther proximally than the core such that a proximal end of the core terminates at a distal section of the second tube.

Clause 13. The intravascular device of clause 12, wherein at least a portion of a lumen of the second tube contains a filler.

Clause 14. The intravascular device of clause 13, wherein the portion of the lumen of the second tube containing the filler is not coincident with the core.

Clause 15. The intravascular device of clause 13 or clause 14, wherein the filler comprises a polymer.

Clause 16. The intravascular device of clause 15, wherein the filler comprises polyether block amide.

Clause 17. The intravascular device of any one of clauses 13 through 16, wherein the filler has an elastic modulus of 1 MPa to 1000 MPa, or 100 MPa to 900 MPa, or 200 MPa to 800 MPa, or 300 MPa to 700 MPa, or 400 MPa to 600 MPa, or 500 MPa.

Clause 18. The intravascular device of any one of clauses 13 through 17, wherein the filler comprises a metal.

Clause 19. The intravascular device of any one of clauses 10 through 18, wherein the first tube and the second tube contact each other at a joint, and wherein a proximal end of the core is disposed 0.5 cm to 5 cm proximal of the joint.

Clause 20. The intravascular device of clause 19, wherein an adhesive is disposed at the joint.

Additional Terms & Definitions

As used herein, the term "longitudinally coincident" (sometimes shortened to simply "coincident") means two components that are both disposed at a given longitudinal position of the device and may, for example, overlap at least partially. For example, if a first component and a second component are longitudinally coincident, at least a portion of the first component overlaps with at least a portion of the second component at some location of the device.

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may also include properties and/or features (e.g., ingredients, components, members, elements, parts, and/or portions) described in one or more separate embodiments and are not necessarily limited strictly to the features expressly described for that particular embodiment. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. An intravascular device, comprising:

a core comprising a proximal section and a distal section, wherein at least a portion of the distal section of the core has a smaller diameter than the proximal section of the core;

a first tube comprising a proximal section and a distal section, wherein the first tube is coupled to the core such that the distal section of the core passes into and is encompassed by the first tube, the first tube comprising a pattern of fenestrations configured to promote flexibility of the first tube while maintaining outer circumferential structure for transmitting torque, the first tube being formed from a first material; and a second tube having substantially the same outer diameter as the first tube, wherein the second tube is coupled to the core such that the proximal section of the core passes into and is encompassed by the second tube, the second tube being formed from a second material, wherein the second tube extends over at least 50% of the length of the proximal section of the core, wherein the second tube extends farther proximally than the core such that a proximal end of the core terminates at a distal section of the second tube and leaves an open proximal lumen at a proximal section of the second tube;

wherein the second material has a lower elastic modulus than the first material.

2. The intravascular device of claim 1, wherein the second tube extends over at least 75% of the length of the proximal section of the core.

3. The intravascular device of claim 1, wherein the second tube extends over substantially the complete length of the proximal section of the core.

4. The intravascular device of claim 1, wherein at least a portion of the proximal section of the first tube passes into and is encompassed by the second tube.

5. The intravascular device of claim 1, wherein the second tube comprises a polymer.

6. The intravascular device of claim 1, wherein the second tube is laminated to the proximal section of the core.

7. The intravascular device of claim 1, wherein the second tube has a variable inner diameter.

8. The intravascular device of claim 7, wherein the variable inner diameter is larger at a proximal section of the second tube and smaller at a distal section of the second tube.

9. The intravascular device of claim 1, wherein the second tube is formed from a metal.

10. The intravascular device of claim 1, wherein a portion of the open proximal lumen of the second tube contains a polymer filler.

11. The intravascular device of claim 10, wherein the filler has an elastic modulus of 1 MPa to 1000 MPa.

12. The intravascular device of claim 10, wherein the filler comprises a metal.

13. The intravascular device of claim 9, wherein the first tube and the second tube contact each other at a joint, and wherein a proximal end of the core is disposed 0.5 cm to 5 cm proximal of the joint.

14. The intravascular device of claim 13, wherein an adhesive is disposed at the joint.

15. An intravascular device, comprising:

a core comprising a proximal section and a distal section, wherein at least a portion of the distal section of the core has a smaller diameter than the proximal section of the core;

a first tube comprising a proximal section and a distal section, wherein the first tube is coupled to the core such that the distal section of the core passes into and is encompassed by the first tube, the first tube comprising a pattern of fenestrations configured to promote flexibility of the first tube while maintaining outer circumferential structure for transmitting torque, the first tube being formed from a first material; and a second tube having substantially the same outer diameter as the first tube, wherein the second tube is coupled to the core such that the proximal section of the core passes into and is encompassed by the second tube without any space between an outer surface of the proximal section of the core and an inner surface of the second tube, the second tube being formed from a second material, wherein the second tube extends over substantially the complete length of the proximal section of the core, wherein the second tube extends farther proximally than the core such that a proximal end of the core terminates at a distal section of the second tube and leaves an open proximal lumen at a proximal section of the second tube;

wherein the second tube has a variable inner diameter, and wherein the second tube has a lower elastic modulus than the first tube.

16. An intravascular device, comprising:

a core comprising a proximal section and a distal section;

a first tube comprising a proximal section and a distal section, wherein the first tube is coupled to the core such that the distal section of the core passes into and is encompassed by the first tube, the first tube comprising a pattern of fenestrations; and a second tube having substantially the same outer diameter as the first tube, wherein the second tube is coupled to the core such that the proximal section of the core passes into and is encompassed by the second tube, wherein the second tube extends farther proximally than the core such that a proximal end of the core terminates at a distal section of the second tube and leaves an open proximal lumen at a proximal section of the second tube, wherein the proximal lumen of the second tube contains a polymer filler and/or a metal filler.

17. The intravascular device of claim 16, wherein the filler has an elastic modulus of 1 MPa to 1000 MPa.

18. The intravascular device of claim 16, wherein the second tube comprises a polymer.

19. The intravascular device of claim 16, wherein the first tube is formed from a first material and the second tube is formed from a second material, and wherein the second material has a lower elastic modulus than the first material.

* * * * *